(12) United States Patent
Shishido et al.

(10) Patent No.: US 12,726,458 B2
(45) Date of Patent: Sep. 1, 2026

(54) SPECIMEN INSPECTION AUTOMATION SYSTEM AND FIXED POSITION INFORMATION ALLOCATION METHOD

(71) Applicant: HITACHI HIGH-TECH CORPORATION, Tokyo (JP)

(72) Inventors: Daigo Shishido, Tokyo (JP); Kuniaki Onizawa, Tokyo (JP)

(73) Assignee: HITACHI HIGH-TECH CORPORATION, Tokyo (JP)

( * ) Notice: Subject to any disclaimer, the term of this patent is extended or adjusted under 35 U.S.C. 154(b) by 329 days.

(21) Appl. No.: 18/698,035

(22) PCT Filed: Sep. 26, 2022

(86) PCT No.: PCT/JP2022/035688
§ 371 (c)(1),
(2) Date: Apr. 3, 2024

(87) PCT Pub. No.: WO2023/079861
PCT Pub. Date: May 11, 2023

(65) Prior Publication Data

US 2024/0420832 A1 Dec. 19, 2024

(30) Foreign Application Priority Data

Nov. 5, 2021 (JP) ................................ 2021-180829

(51) Int. Cl.
*H04L 61/5038* (2022.01)
*H04L 61/50* (2022.01)
(Continued)

(52) U.S. Cl.
CPC .......... *H04L 61/5038* (2022.05); *H04L 61/50* (2022.05); *H04L 61/5007* (2022.05); *G16H 40/40* (2018.01)

(58) Field of Classification Search
CPC . H04L 61/5038; H04L 61/50; H04L 61/5007; G16H 40/40; G01N 2035/00326; G01N 2035/00881; G01N 35/00871
See application file for complete search history.

(56) References Cited

U.S. PATENT DOCUMENTS 11,863,374 B2 * 1/2024 Hasegawa ........... H04L 41/0686
2016/0205066 A1 * 7/2016 Attarwala ........... H04L 61/5038 709/208
2021/0111924 A1 4/2021 Yamashina et al.

FOREIGN PATENT DOCUMENTS

EP 3683583 A1 * 7/2020 ............. G01N 27/62
EP 2856150 B1 * 4/2022 ....... G01N 35/00732
(Continued)

OTHER PUBLICATIONS

Internatinal Search Report of PCT/JP2022/035688 dated Dec. 6, 2022.

*Primary Examiner* — Thomas Randazzo
(74) *Attorney, Agent, or Firm* — MATTINGLY & MALUR, PC

(57) ABSTRACT

In order to enable easy setting of a configuration of a specimen inspection automation system, the present disclosure proposes a technique for automatically allocating an IP address (unique position information) to each unit constituting the specimen inspection automation system. For example, the present disclosure proposes a specimen inspection automation system comprising: a plurality of slave station devices each of which corresponds to at least one of a transport device for transporting a specimen and an analyzer for analyzing the specimen; and a master station device that communicates with the slave station devices through a communication line and controls the slave station devices. The master station device performs a process for allocating unique position information to each of the slave
(Continued)

station devices by using information acquired through communication with the slave station devices.

12 Claims, 9 Drawing Sheets

(51) Int. Cl.
*H04L 61/5007* (2022.01)
*G16H 40/40* (2018.01)

(56) References Cited

FOREIGN PATENT DOCUMENTS

| | | | | | |
|---|---|---|---|---|---|
| JP | 2003-273925 | A | | 9/2003 | |
| JP | 2006-148813 | A | | 6/2006 | |
| JP | 2008-252637 | A | | 10/2008 | |
| JP | WO-2011040203 | A1 | * | 4/2011 | ........... G01N 35/026 |
| JP | 2017-138131 | A | | 8/2017 | |
| JP | 2018-019199 | A | | 2/2018 | |
| JP | 2019-161364 | A | | 9/2019 | |

* cited by examiner

[FIG. 1A]
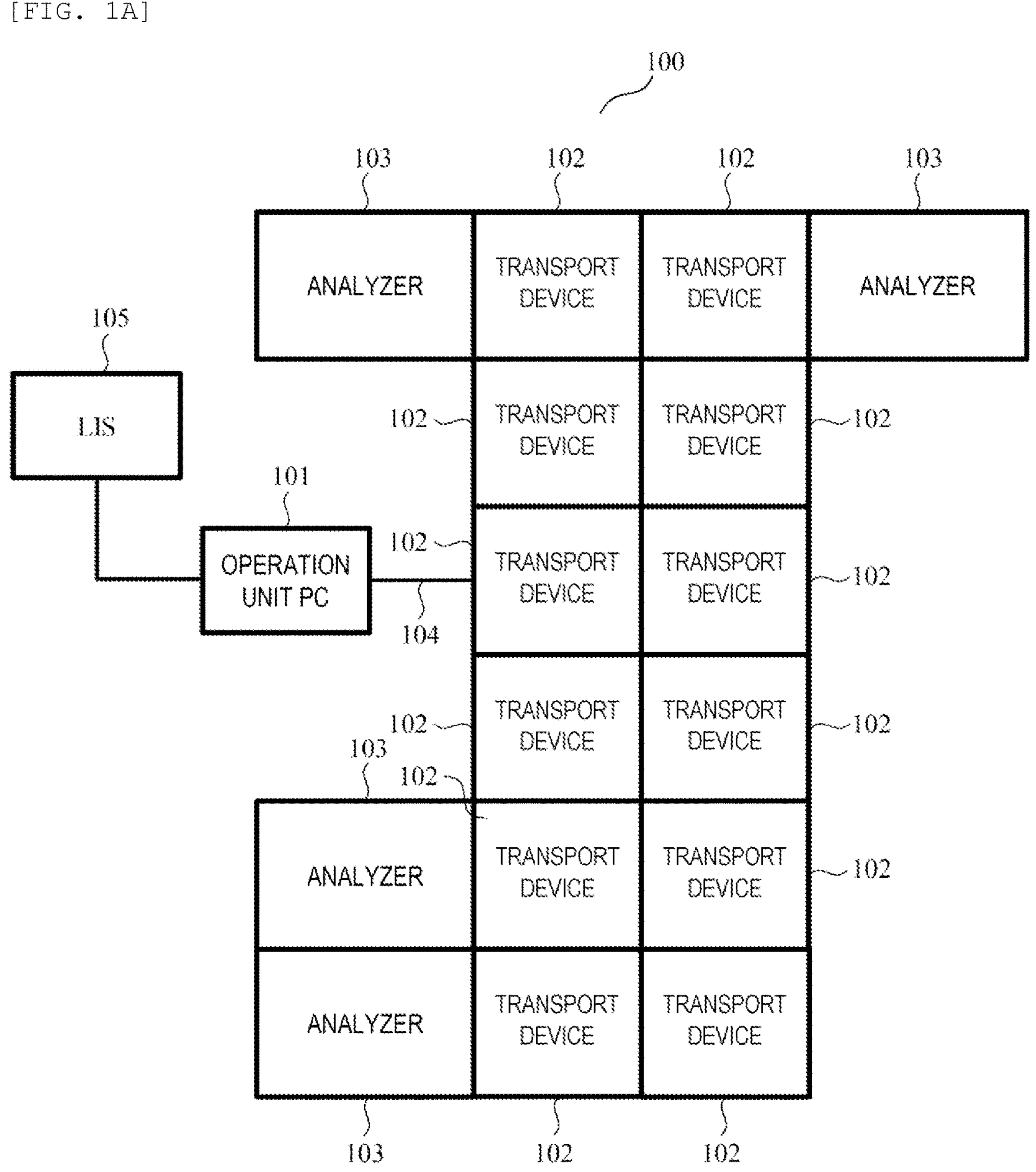

[FIG. 1B]
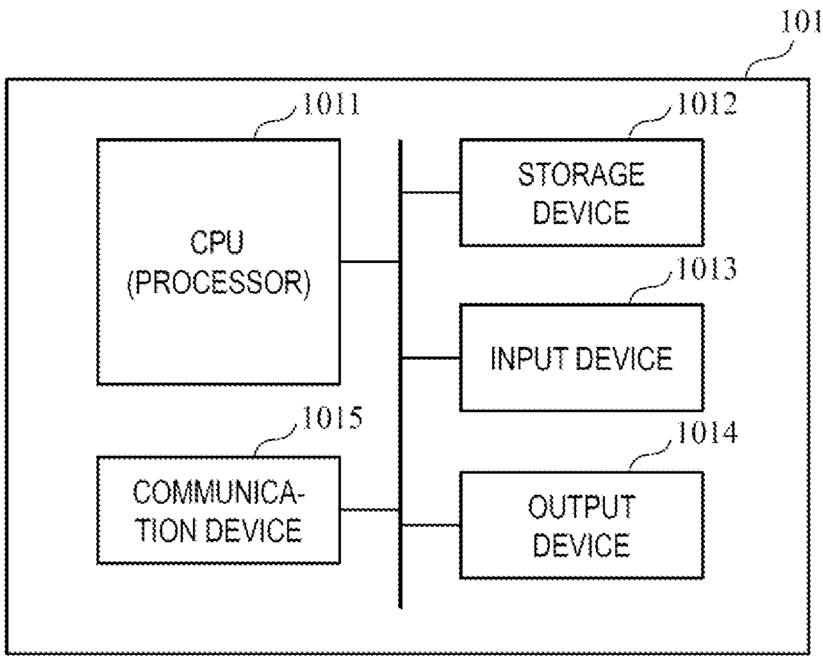
[FIG. 1C]
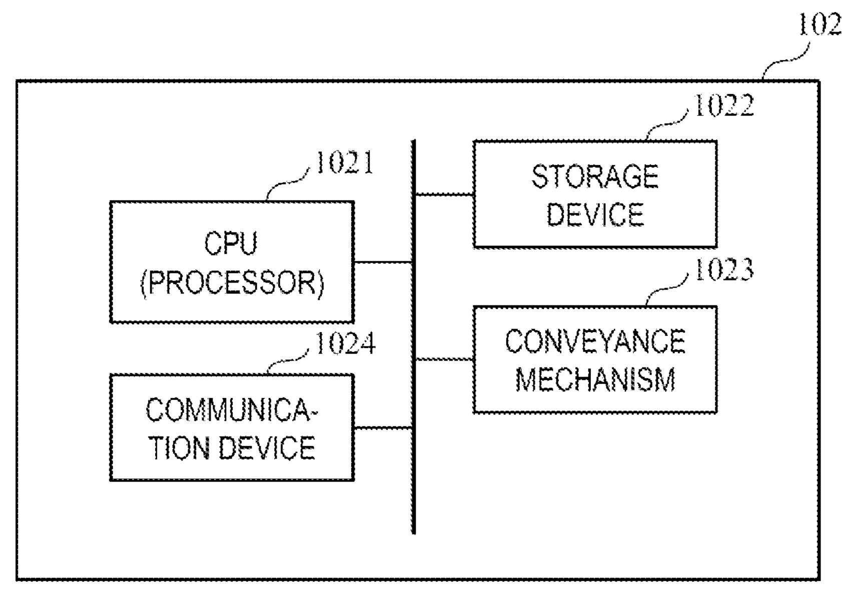

[FIG. 1D]
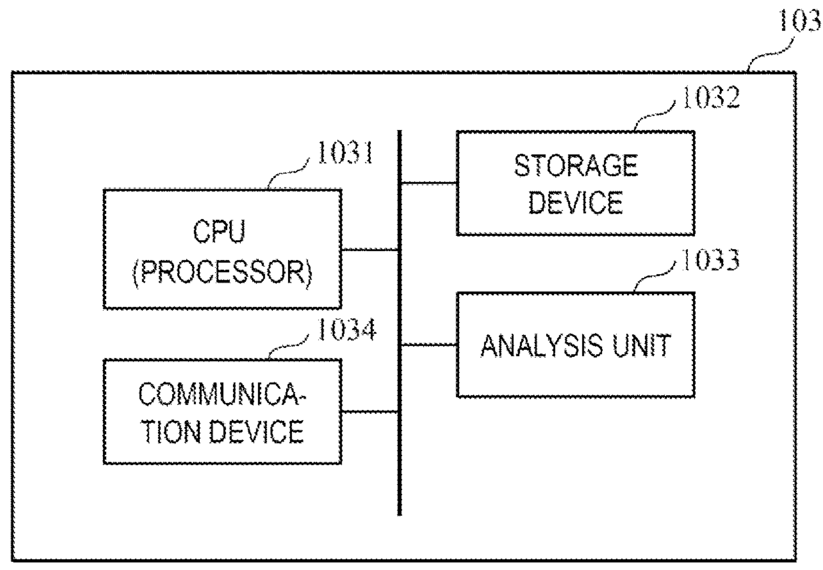
[FIG. 2]
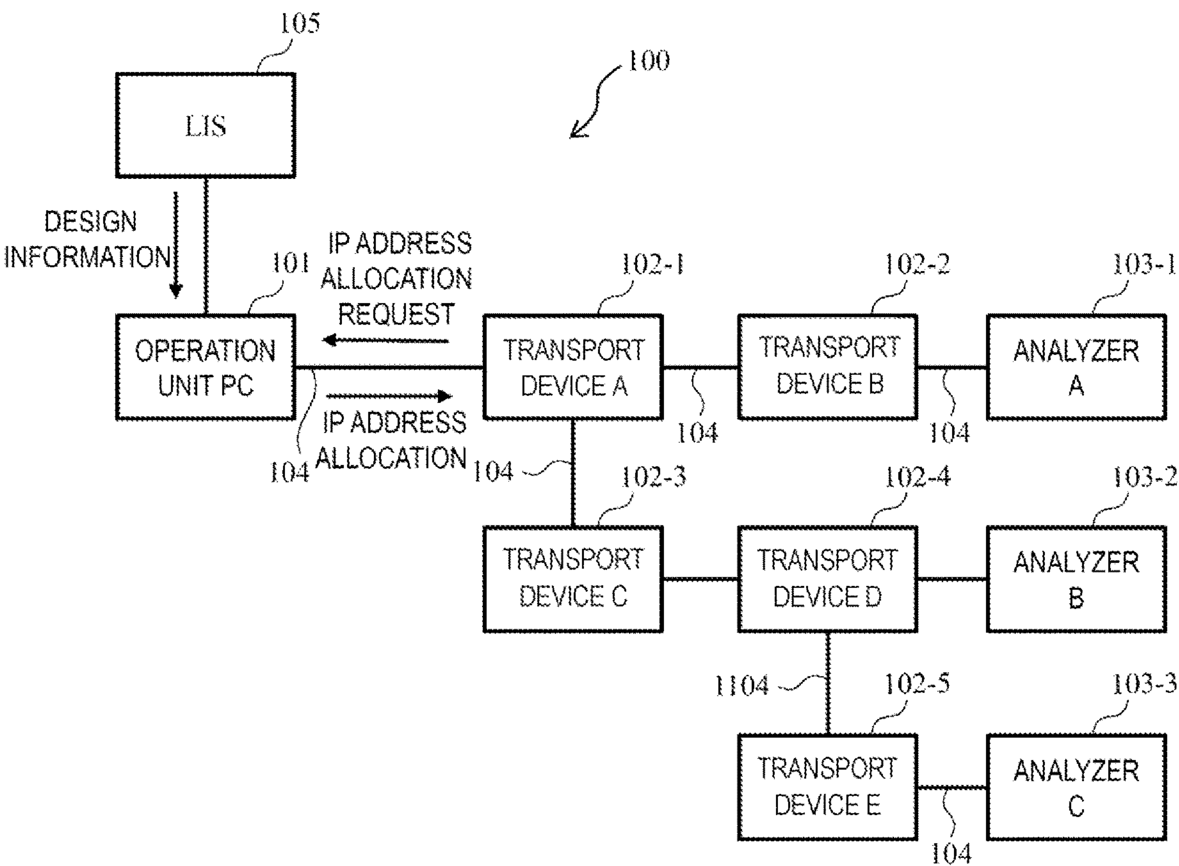

[FIG. 3]

| PRIORITY ORDER | UNIT NAME (UNIT IDENTIFICATION INFORMATION) | IP ADDRESS |
|---|---|---|
| 1 | TRANSPORT DEVICE A | 1 |
| 2 | TRANSPORT DEVICE B | 2 |
| 3 | TRANSPORT DEVICE C | 3 |
| 4 | ANALYZER A | 4 |
| : | : | : |
| : | : | : |

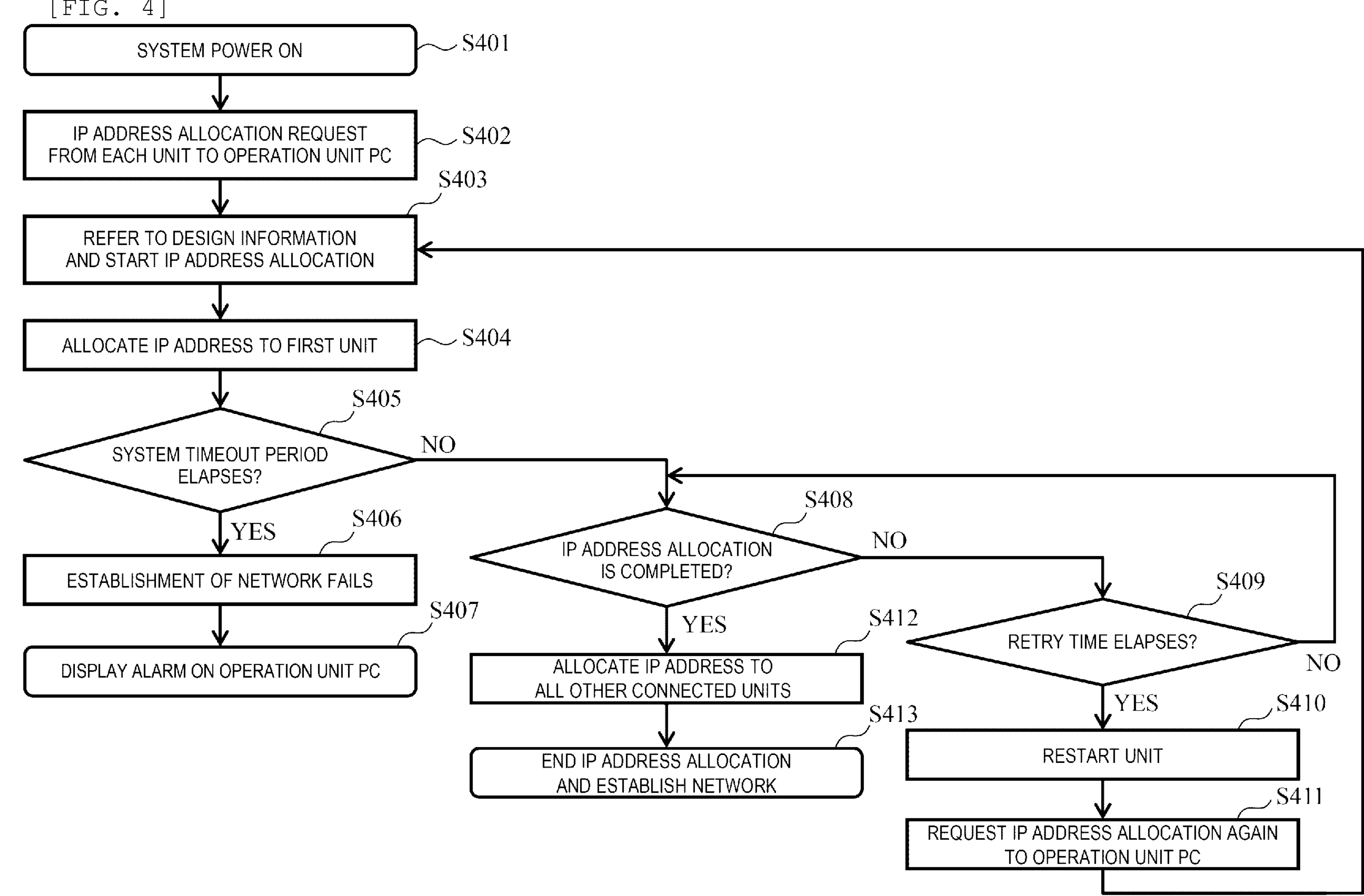
[FIG. 4]
SYSTEM POWER ON
S401
IP ADDRESS ALLOCATION REQUEST FROM EACH UNIT TO OPERATION UNIT PC
S402
REFER TO DESIGN INFORMATION AND START IP ADDRESS ALLOCATION
S403
ALLOCATE IP ADDRESS TO FIRST UNIT
S404
SYSTEM TIMEOUT PERIOD ELAPSES?
S405
NO
YES
ESTABLISHMENT OF NETWORK FAILS
S406
DISPLAY ALARM ON OPERATION UNIT PC
S407
IP ADDRESS ALLOCATION IS COMPLETED?
S408
NO
YES
ALLOCATE IP ADDRESS TO ALL OTHER CONNECTED UNITS
S412
END IP ADDRESS ALLOCATION AND ESTABLISH NETWORK
S413
RETRY TIME ELAPSES?
S409
NO
YES
RESTART UNIT
S410
REQUEST IP ADDRESS ALLOCATION AGAIN TO OPERATION UNIT PC
S411

[FIG. 5]
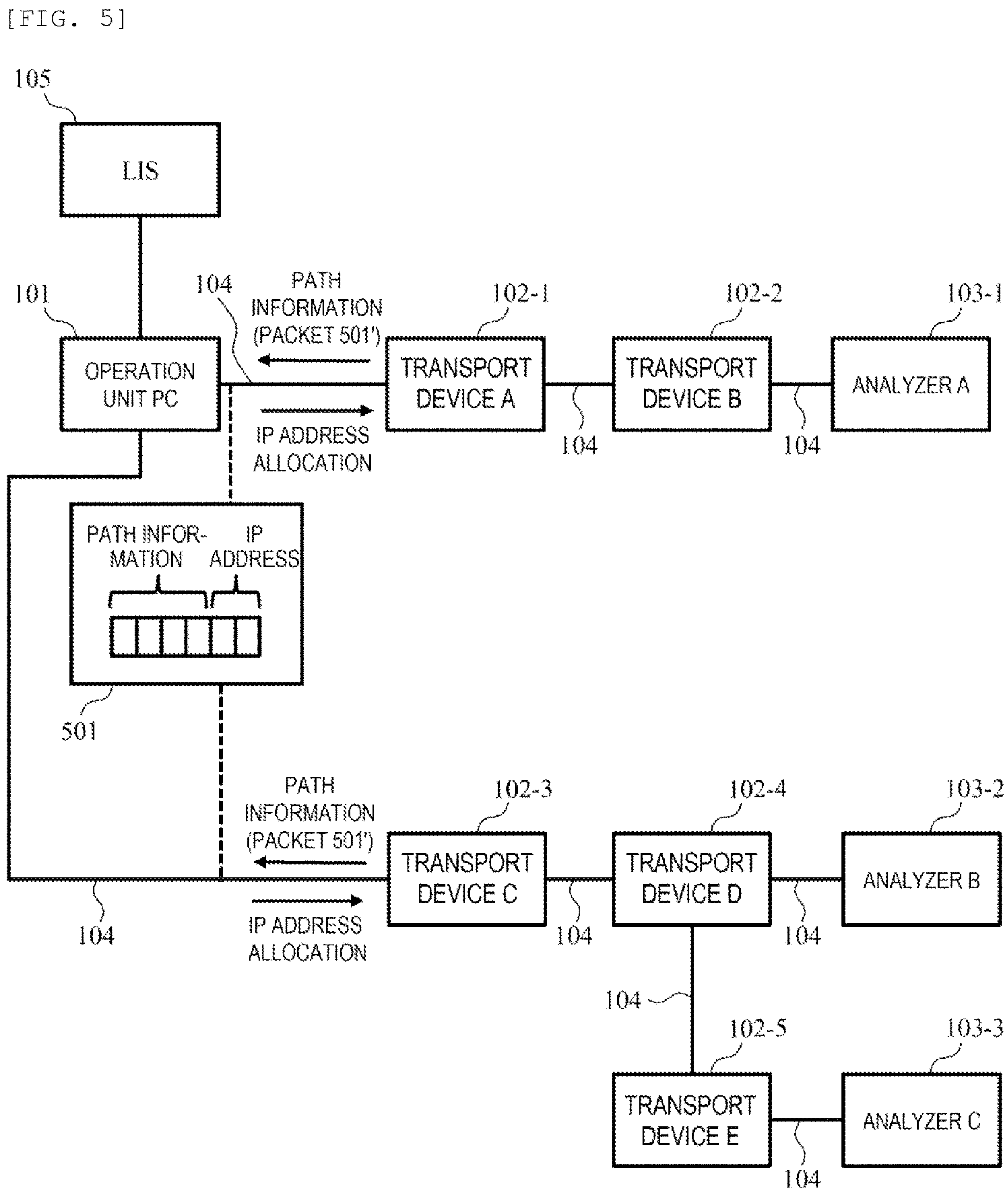

[FIG. 6]

| PATH INFORMATION | IP ADDRESS | PORT NAME | PORT NUMBER |
|---|---|---|---|
| 21 | 1 | (EMPTY) | 0 |
| 221 | 2 | SATELLITE ITSELF | 1 |
| 2221 | 3 | DN1 | 2 |
| 2231 | 4 | DN2 | 3 |
| : | : | DN3 | 4 |
| : | : | : | : |
| | | : | : |

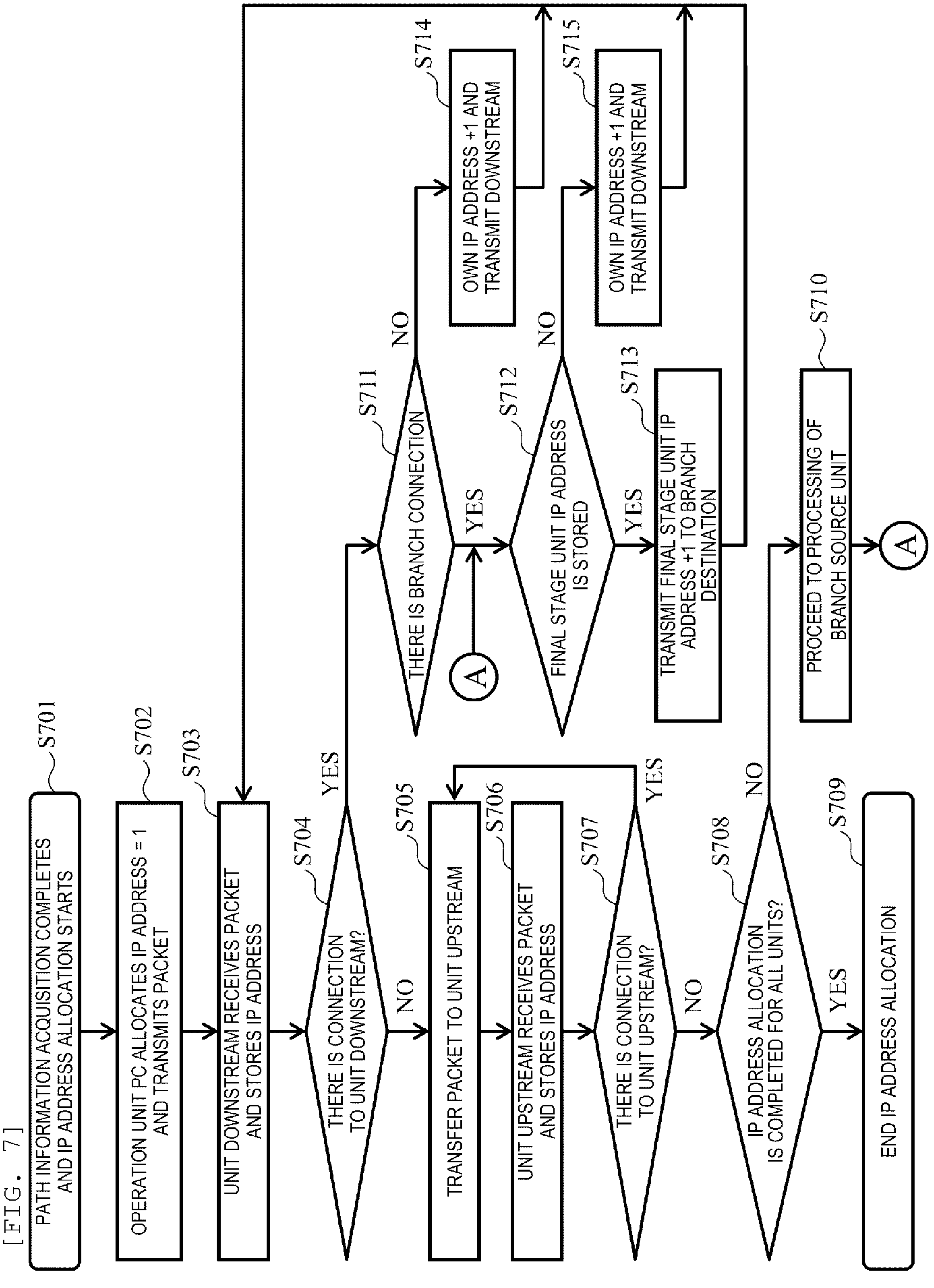
[FIG. 7]
PATH INFORMATION ACQUISITION COMPLETES AND IP ADDRESS ALLOCATION STARTS
S701
OPERATION UNIT PC ALLOCATES IP ADDRESS = 1 AND TRANSMITS PACKET
S702
UNIT DOWNSTREAM RECEIVES PACKET AND STORES IP ADDRESS
S703
THERE IS CONNECTION TO UNIT DOWNSTREAM?
S704
YES
NO
TRANSFER PACKET TO UNIT UPSTREAM
S705
UNIT UPSTREAM RECEIVES PACKET AND STORES IP ADDRESS
S706
THERE IS CONNECTION TO UNIT UPSTREAM?
S707
YES
NO
IP ADDRESS ALLOCATION IS COMPLETED FOR ALL UNITS?
S708
NO
YES
END IP ADDRESS ALLOCATION
S709
THERE IS BRANCH CONNECTION
S711
NO
YES
A
OWN IP ADDRESS +1 AND TRANSMIT DOWNSTREAM
S714
FINAL STAGE UNIT IP ADDRESS IS STORED
S712
NO
YES
OWN IP ADDRESS +1 AND TRANSMIT DOWNSTREAM
S715
TRANSMIT FINAL STAGE UNIT IP ADDRESS +1 TO BRANCH DESTINATION
S713
PROCEED TO PROCESSING OF BRANCH SOURCE UNIT
S710
A

[FIG. 8]
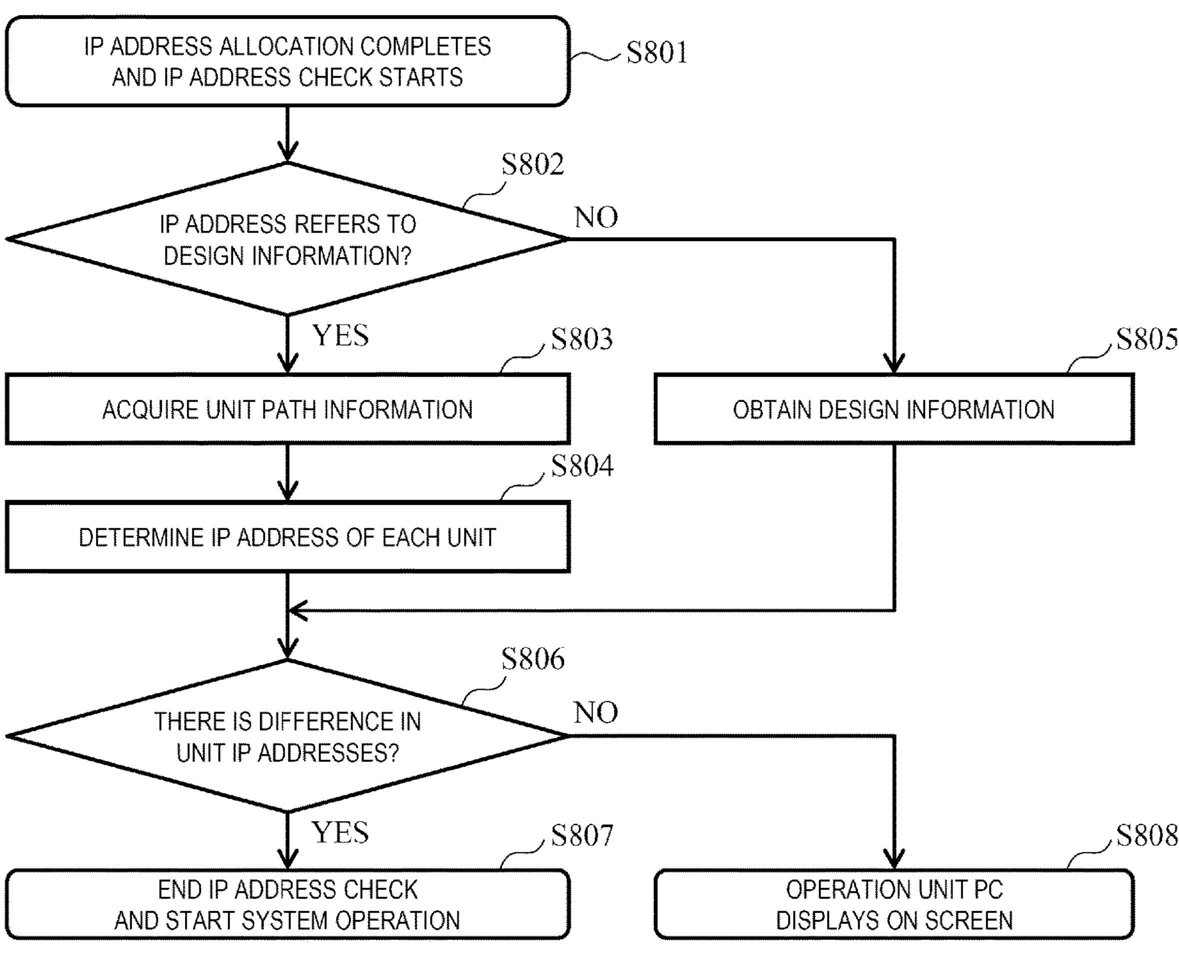

SPECIMEN INSPECTION AUTOMATION SYSTEM AND FIXED POSITION INFORMATION ALLOCATION METHOD

TECHNICAL FIELD

The present disclosure relates to a specimen test automation system and a fixed position information allocation method.

BACKGROUND ART

In recent years, automation of specimen tests for diagnosis in a medical field has been advanced. In a specimen test automation system, a system is implemented by combining units having different roles, such as a specimen pretreatment device, a transport device, a biochemical analyzer, and an immunological analyzer. When introducing the specimen test automation system, a user can construct the system by freely combining the units, and can flexibly cope with a need of a facility where the system is introduced to some extent.

When the system is implemented, to correctly control each unit, an IP address is fixedly allocated for each unit in a current product. By using the allocation of the IP address and LAN, an operation unit PC and a control target unit are network-connected, and in this state, software of the operation unit PC operates to control the unit. For fixed IP address allocation, for example, there is a method of fixedly setting an IP address by hardware using a dip switch or the like on a substrate.

For example, PTL 1 discloses, regarding fixed IP address allocation, "a distributed control system including: a central processing device; a central communication device; a plurality of terminal communication devices each having at least one controlled device connected thereto; an information storage device; and a network having a tree structure including a plurality of communication paths between the central communication device and the terminal communication devices, a plurality of communication paths between the terminal communication devices, and a plurality of communication paths between the terminal communication devices and the information storage device, in which the central communication device is provided with a normal communication port, the terminal communication devices are each provided with a communication port upstream and a communication port downstream, the information storage device is provided with a device information communication port, and the network is provided with a first communication path for connecting a communication port upstream of a terminal communication device with a communication port downstream of a terminal communication device and for connecting a communication port upstream of a terminal communication device with the normal communication port of the central communication device, and a second communication path for connecting between communication ports downstream of the terminal communication devices positioned at edges of the network and for connecting communication ports downstream of the terminal communication devices, with the device information communication port of the information storage device."

For example, PTL 2 discloses, regarding fixed IP address allocation, "an information transmission system for transmitting same information from a master station to a plurality of slave stations via a network, in which the master station includes a control unit that performs processing of transmitting same information to the plurality of slave stations by multicast using a multicast router and retransmitting the information by unicast to a slave station that does not receive delivery confirmation from the slave station, a transmission processing unit, a reception processing unit that receives the delivery confirmation, and a database, and the slave station includes an information processing unit that receives information from the master station and transmits the delivery confirmation to the master station, and a transmission and reception unit."

CITATION LIST

Patent Literature

PTL 1: JP2019-161364A
PTL 2: JP2003-273925A

SUMMARY OF INVENTION

Technical Problem

According to the specimen test automation system in the related art (fixed IP address allocation) disclosed in the PTLs, the system can be constructed flexibly to some extent, but the number of units, types, and combination patterns are increased. Therefore, in a case of the fixed IP address allocation, it is necessary to individually set the dip switch described above for each unit before a network connection, which is complicated for a service person when installing the device. Thus, in a specimen test automation system adopting a distributed control method, it is necessary to further facilitate system construction while maintaining flexibility to cope with a wide range of system configuration construction.

In view of such a situation, the present disclosure proposes a technique capable of easily setting a configuration of a specimen test automation system.

Solution to Problem

To solve the above problem, the present disclosure proposes a technique of automatically allocating an IP address (unique position information) to each unit constituting a specimen test automation system. For example, the present disclosure proposes a specimen test automation system including: a plurality of slave station devices each corresponding to at least one of a transport device that transports a specimen and an analyzer that analyzes the specimen; and a master station device configured to communicate with the plurality of slave station devices via a communication path and control the plurality of slave station devices. The master station device executes, using information acquired by communicating with each of the plurality of slave station devices, processing of allocating unique position information to each of the plurality of slave station devices.

Additional features related to the present disclosure will be clarified based on the description of the present description and the accompanying drawings. Aspects of the present disclosure may be achieved and implemented using elements, combinations of various elements, the following detailed description, and accompanying claims.

It is necessary to understand that the description of the present description is merely a typical example, and does not limit the scope of the claims or applications of the present disclosure in any way.

Advantageous Effects of Invention

According to the present disclosure, it is possible to automatically allocate an ID to each unit constituting the specimen test automation system and to set a system configuration easily and automatically.

BRIEF DESCRIPTION OF DRAWINGS

FIG. 1A is a diagram showing a schematic configuration example of a specimen test automation system 100 according to the present embodiment, and is a schematic configuration diagram of a specimen test automation system.

FIG. 1B is a diagram showing an example of an internal schematic configuration of an operation unit PC 101, which is a master station device.

FIG. 1C is a diagram showing an example of an internal schematic configuration of a transport device 102, which is a slave station device.

FIG. 1D is a diagram showing an example of an internal schematic configuration of an analyzer 103, which is another slave station device.

FIG. 2 is a diagram showing an example of a system configuration of an IP address allocation target, and an example of a connection configuration of the operation unit PC (master station device) 101 and a plurality of units (slave station devices: transport devices 102_1 to n and analyzers 103_1 to m; n and m are any integers).

FIG. 3 is a diagram showing a configuration example of an IP address table (also referred to as "design information" on the specimen test automation system 100) held by an LSI 105.

FIG. 4 is a flowchart for showing processing according to an IP address allocation method 1.

FIG. 5 is a diagram showing an example of a system configuration of the IP address allocation target, and an example of a connection configuration of the operation unit PC (master station device) 101 and a plurality of units (slave station devices: transport devices 102_1 to n and analyzers 103_1 to m; n and m are any integers).

FIG. 6 is a diagram showing a part of a path information table acquired by path information acquisition processing.

FIG. 7 is a flowchart showing IP address allocation processing according to an IP address allocation method 2.

FIG. 8 is a flowchart showing details of IP address consistency check processing.

DESCRIPTION OF EMBODIMENTS

The present embodiment relates to a specimen test automation system including, for example, a plurality of slave station devices (for example, transport devices and various analyzers) and a master station device (management device (computer: operation unit PC)) that manages and controls the slave station devices, the specimen test automation system being implemented by combining a plurality of slave stations, in which the master station device and each slave station device perform communication, and the master station device executes, based on predetermined information acquired from the slave station device, processing of allocating an IP address (position information on a network of the slave station device or position information on the specimen test automation system) to each slave station device. In the present embodiment, as an IP address allocation method, a method of referring to IP address allocation information (IP address table: see FIG. 3) held by the master station device (IP address allocation method 1) and a method of not referring to the IP address allocation information (IP address allocation method 2) are proposed.

Hereinafter, an embodiment of the present disclosure will be described with reference to the accompanying drawings. In the accompanying drawings, functionally the same elements may be denoted by the same reference signs. The accompanying drawings show specific embodiments and implementation examples according to the principle of the present disclosure, but these are for understanding the present disclosure and are by no means to be used to limit the present disclosure.

The present embodiment is described in sufficient detail for a person skilled in the art to implement the present disclosure, but it is to be understood that other implementations and aspects are possible, and changes in configuration and structure and replacement of various elements are possible without departing from the scope and spirit of the technical idea of the present disclosure. Therefore, the following description is not to be construed as being limited thereto.

As will be described later, the embodiment of the present disclosure may be implemented by software operating on a general-purpose computer, or may be implemented by dedicated hardware or a combination of software and hardware.

In the following description, each piece of information according to the present disclosure may be described in the form of a "table", but the information may not necessarily be expressed in a data structure based on a table, and may be expressed in a data structure such as a list, a DB, and a queue or in other forms. Therefore, to indicate that the information does not depend on the data structure, "table", "list", "DB", "queue", and the like may be simply referred to as "information".

In describing contents of each piece of information, expressions such as "identification information", "identifier", "first name", "name", and "ID" can be used, and these expressions can be replaced with each other.

(1) IP Address Allocation Method 1

The IP address allocation method 1 is a method in which, in response to an IP address allocation request from the slave station device (a unit: a transport device and various analyzers), an operation unit PC (management device), which is a master station device, automatically allocates an IP address to each slave station device according to an IP address table (information that defines an IP address and an allocation priority order of each unit). Hereinafter, a system configuration example, IP address allocation processing, and the like will be described in detail using a specimen test automation system as an example.

<Configuration Example of Specimen Test Automation System and Overview of Operation During Specimen Test>

(i) System Configuration Example

FIG. 1A is a diagram showing a schematic configuration example of a specimen test automation system 100 according to the present embodiment. The specimen test automation system 100 includes an operation unit PC (also referred to as a management device) 101, a plurality of transport devices 102 that transport a holder or an empty holder in which a specimen such as blood or urine is installed, and various analyzers 103. There are two types of analyzers: a biochemical analyzer and an immunological analyzer. A purpose of use is determined by each analysis item. The system can be implemented by combining a biochemical analyzer and an immunological analyzer.

When a specimen is loaded into a specimen loading portion (not shown) of the specimen test automation system 100, specimen specifying information (information on a person from whom the specimen is collected, a date and time of collection, a type of the specimen, an amount of the specimen, and the like) is read by a reader (for example, a barcode reader or an RFID reader) (not shown) disposed in a specimen transport path. The read specimen specifying information is transferred to the operation unit PC 101. The operation unit PC 101 searches for request information regarding the specimen to be tested, and when there is no request information, the operation unit PC 101 makes an inquiry to a laboratory information system (LIS) 105, which is a laboratory host, and obtains request information for test. The operation unit PC 101 determines which unit to stop by or which unit to skip based on the obtained request information.

In the specimen test automation system 100, the operation unit PC 101 and the units 102 and 103 are connected by an Ethernet cable 104. A configuration of pin arrangements of connection ports of the Ethernet cables 104 in the units 102 and 103 are the same, and cross cables are adopted as the cables to be used. Transmission terminals can be connected by using a cable other than the cross cable, but by adopting the cross cable, when the cables are connected to each other, the transmission terminals are prevented from being connected to each other, and communication can be performed even when the transmission terminals are connected to any port without collision of signals.

Software for controlling the entire specimen test automation system 100 is installed in the operation unit PC 101. When controlling the target units 102 and 103, the software uses the IP address and a network established by the Ethernet cable connection.

(ii) Overview of Operation of Specimen Test Automation System 100

A distributed control method is introduced into the specimen test automation system 100 according to the present embodiment. In the distributed control method, the specimen test automation system 100 includes a host computer (LIS 105), the master station device (operation unit PC 101) connected to the host computer, and the plurality of slave station devices (a transport device 102 and an analyzer 103) including digital input and output ports, and the network is implemented by the master station device and the plurality of slave station devices in a form such as multi-drop or daisy chain. In the distributed control method, the master station device and the plurality of slave station devices communicate with each other in a first communication mode and a second communication mode, and can switch between the first communication mode and the second communication mode. Here, the first communication mode is a mode in which serial data transmitted from the operation unit PC 101, the other transport device 102, or analyzer 103 via the Ethernet cable 104 serving as a communication path is received in bit units, and the serial data is transmitted to the other transport device 102 or analyzer 103 downstream via the Ethernet cable 104. The second communication mode is a mode in which serial data transmitted from the transport device 102 or the analyzer 103 via the Ethernet cable 104 is received in packet units and then transmitted to the operation unit PC 101 or the transport device 102 or the analyzer 103 upstream via the Ethernet cable 104.

In the first communication mode, the operation unit PC 101 transfers a control command to the transport device 102 and the analyzer 103 via the Ethernet cable 104, and performs a specimen transport operation or a specimen dispensing operation. In the second communication mode, the transport device 102 and the analyzer 103 transmit information on an operation status of the transport device 102 and the analyzer 103 (each unit) during a system operation (a normal operation, error occurrence, and the like) to the operation unit PC 101 via the Ethernet cable 104.

When an abnormality occurs in the transport device 102 or the analyzer 103 constituting the specimen test automation system 100 and communication from upstream to downstream is blocked in the middle of a communication path, the operation unit PC 101 can switch a communication direction from downstream to upstream in the second communication mode. Accordingly, the communication can be continued while bypassing an abnormal unit. A continuous operation of the system operation in the second communication mode is merely an example, and depending on a test situation, the entire system operation may be stopped, and device replacement or component replacement may be performed by a service person.

<Examples of Internal Schematic Configurations of Master Station Device and Slave Station Device>

(i) Example of Internal Schematic Configuration of Operation Unit PC (Master Station Device) 101

FIG. 1B is a diagram showing an example of an internal schematic configuration of the operation unit PC 101, which is the master station device. The operation unit PC 101 is implemented by a general computer, and includes, for example, a CPU (processor) 1011, a storage device 1012 that stores an operation program executed by the operation unit PC 101 and various types of parameters and data used for processing by the operation unit PC 101, an input device 1013, an output device 1014, and a communication device 1015.

The CPU 1011 reads, from the storage device 1012, various programs (for example, programs for executing processing to be handled by the operation unit PC 101 in flowcharts shown in FIG. 4, FIG. 7, and FIG. 8 to be described later), loads the programs in an internal memory (not shown), and executes the various programs.

The input device 1013 is implemented by, for example, a keyboard or a mouse for an operator (user) to input an instruction and data. The output device 1014 is implemented by, for example, a display device or a printer for outputting a processing result or the like. The communication device 1015 is, for example, a device that communicates with each unit (the transport device 102 and the analyzer 103) in the first and second communication modes, and has a plurality of communication ports (for example, four ports).

(ii) Example of Internal Schematic Configuration of Transport Device (Slave Station Device) 102

FIG. 1C is a diagram showing an example of an internal schematic configuration of the transport device 102, which is the slave station device. The transport device 102 includes, for example, a CPU (processor) 1021, a storage device 1022 that stores an operation program executed by the transport device 102 and various types of parameters and data used for processing by the transport device 102, a transport mechanism 1023, and a communication device 1024.

The CPU 1021 reads, from the storage device 1022, various programs (for example, programs for executing processing to be handled by the transport device 102 in the flowcharts shown in FIG. 4, FIG. 7, and FIG. 8 to be described later), loads the programs in an internal memory (not shown), and executes the various programs.

The transport mechanism 1023 includes a path for transporting a specimen and a drive device for driving the path. The communication device 1024 is a device that communicates with another unit (another slave station device or the master station device) in the first and second communication modes, and has a plurality of communication ports (for example, four ports).

(iii) Example of Internal Schematic Configuration of Analyzer (Slave Station Device) 103

FIG. 1D is a diagram showing an example of an internal schematic configuration of the analyzer 103, which is another slave station device. The analyzer 103 includes, for example, a CPU (processor) 1031, a storage device 1032 that stores an operation program executed by the analyzer 103 and various types of parameters and data used for processing by the analyzer 103, an analysis unit 1033, and a communication device 1034.

The CPU 1031 reads, from the storage device 1032, various programs (for example, programs for executing processing to be handled by the analyzer 103 in the flowcharts shown in FIG. 4, FIG. 7, and FIG. 8 to be described later), loads the programs in an internal memory (not shown), and executes the various programs.

The analysis unit 1033 includes components (for example, a centrifugal separation mechanism, an optical analysis mechanism, a chromatograph unit, and an electrophoresis unit) for analyzing a specimen. The communication device 1034 is a device that communicates with another unit (another slave station device or the master station device) in the first and second communication modes, and has a plurality of communication ports (for example, four ports).

<Content of IP Address Allocation Processing 1>

With reference to FIGS. 2 to 4, the IP address allocation processing 1 to each unit (slave station device) after power of the specimen test automation system 100 is turned on is to be described. FIG. 2 is a diagram showing an example of a system configuration of an IP address allocation target, and an example of a connection configuration of the operation unit PC (master station device) 101 and a plurality of units (slave station devices: transport devices A 102_1 to n and analyzers 103_1 to m; n and m are any integers). FIG. 3 is a diagram showing a configuration example of an IP address table (also referred to as "design information" on the specimen test automation system 100) held by the LSI 105. FIG. 4 is a flowchart for showing processing according to the IP address allocation method 1.

(i) Step 401

When the power of the specimen test automation system 100 is ON, AC power supply is started, and the processors (central control units) 1021 and 1031 (hereinafter, referred to as "unit processors") of the transport device 102 and the analyzer 103 start up. The unit processor is in a dedicated FPGA or the like mounted on a motor controller board of the unit, as a control IC.

Regarding the units (the transport device A to E, 102_1 to 102_5, and an analyzer A to C, 103_1 to 103_3) in the specimen test automation system 100 shown in FIG. 2, the closer an arrangement position is to the operation unit PC 101, the more upstream the unit is defined, and the farther the arrangement position is, the more downstream the unit is defined. In a connection of each unit in the specimen test automation system 100, a main path and a sub path branching from the main path (in a case of further branching from the sub path (primary sub path), the sub path is secondary, tertiary, . . . sub path) may be defined in advance, and a unit in the main path may be defined as a unit upstream of a unit in the sub path.

(ii) Step 402

The unit processor transmits an IP address allocation request to the operation unit PC 101 via a connection network in the specimen test automation system 100. For example, the unit processor may form the IP address allocation request by making information for instructing IP address allocation and identification information on the unit (for example, unique device information held by the unit) a packet.

(iii) Step 403

Upon receiving the IP address allocation request (sequentially) from each unit, the operation unit PC 101 approves the request, operates an IP address automatic allocation function, and starts an IP address allocation operation. Specifically, the operation unit PC 101 refers to the IP address table (design information) from the LIS 105 (the design information may be acquired in advance at any timing, stored in the storage device 1012, and referred to), and starts to allocate an IP address according to a priority order in the IP address table. The priority order is stored as the design information in the LIS 105 in advance at the time of system setup. However, the priority order can also be changed according to a change in a layout of the system.

(iv) Step 404

The operation unit PC 101 transmits IP address allocation information to a first unit (a unit with a priority order 1: the transport device A 102_1 in the example of the system configuration in FIG. 2) in the first communication mode. The IP address allocation information is implemented by making, for example, IP address information to be allocated and unit identification information to be allocated a packet. When receiving the IP address allocation information from the operation unit PC 101 via a system network, each unit compares the unit identification information in the IP address allocation information with unit identification information held with confidence, and determines whether the IP address is allocated to the unit itself. When it is determined that the IP address is allocated to the unit itself, the unit holds the IP address. Meanwhile, when it is determined that the IP address is not allocated to the unit itself, the unit ignores the IP address allocation information until reception of the IP address allocation information for the unit itself is confirmed.

(v) Step 405

The operation unit PC 101 determines whether a preset system timeout period elapses. The system timeout period is a time during which the IP address allocation to the allocation target unit is to be completed, and is information for determining that an error occurs if the IP address allocation is not completed within the time.

When the system timeout period elapses (YES in step 405), the processing proceeds to step 406. When the system timeout period does not yet elapse (NO in step 405), the processing proceeds to step 408.

(vi) Steps 406 and 407

The operation unit PC 101 determines that the establishment of the network fails (that is, processing of automatically allocating an IP address to the allocation target unit executed this time fails) (step 406), and outputs an alarm (for example, an alarm display) to the output device (for example, a display screen of a display device) 1014 of the operation unit PC 101.

Thus, when the IP address automatic allocation processing ends in failure, an operator (user) can check the specimen test automation system 100 (for example, each unit and network interconnect in the configuration in FIG. 2) or instruct start of the IP address automatic allocation processing again.

(vii) Step 408

The operation unit PC 101 determines whether the IP address allocation to the allocation target unit (the transport device 102 or the analyzer 103) is completed. Whether the processing is completed can be determined by receiving information indicating that the operation unit PC 101 receives the IP address from the allocation target unit in the second communication mode.

When the IP address allocation to the allocation target unit is completed (YES in step 408), the processing proceeds to step 412. Meanwhile, when the IP address allocation to the allocation target unit is not completed (NO in step 408), the processing proceeds to step 409.

(viii) Step 409

The operation unit PC 101 determines whether a preset retry time (<system timeout period) elapses. When the retry time already elapses (YES in step 409), the processing proceeds to step 410. When the retry time does not yet elapse (NO in step 409), the processing proceeds to step 408, and the IP address allocation processing for the allocation target unit is continued.

(ix) Steps 410 and 411

The allocation target unit executes restart processing (step 410), and transmits an IP address allocation request to the operation unit PC 101 again.

(x) Step 412

The operation unit PC 101 executes the IP address allocation processing for all units (all units downstream of the unit with the priority order 1) other than the unit to which the IP address is first allocated. Specifically, the operation unit PC 101 sequentially executes the processing of step 404 ("first" in step 404 is replaced with "target") to step 411 for a target unit in accordance with the priority order defined in the IP address table (FIG. 3). When the IP address allocation is completed for all the units, the processing proceeds to step 413.

(xi) Step 413

The operation unit PC 101 ends the IP address allocation processing and establishes (activates) a network in the specimen test automation system 100. When the network in the specimen test automation system 100 is established, the operation unit PC 101 can correctly control each unit by issuing an instruction to a specific unit using the IP address.

<Summary of IP Address Allocation Method 1>

(i) As described above, according to the IP address allocation method 1 according to the present embodiment, even when a new transport device and analyzer that is a set with the new transport device are added or when an existing transport device and analyzer that is a set with the existing transport device are replaced, an IP address can be automatically allocated to each unit by turning on the power of the specimen test automation system 100. In the IP address allocation method in the related art, even when there are a plurality of transport devices and analyzers having the same function, dip switches are allocated in advance, so the dip switches are to be disposed at predetermined positions. In the present embodiment, since the IP address is automatically allocated after the transport device and the analyzer are set, when there are a plurality of transport devices or analyzers having the same function, the user can freely dispose each unit without considering disposition positions of each unit. Further, by using a cross cable for a connection of each unit in the present embodiment, it is possible to freely dispose directions of the transport device and the analyzer when a disposition direction is not limited by a hardware configuration such as in a case of a bilaterally symmetrical device configuration. Any method that enables dynamic IP address allocation may be used. A switch (for example, a push button switch) for turning on the power of the specimen test automation system 100 may be pressed by an operator such as a service person, or the switch may be automatically turned on by turning on power of the operation unit PC 101.

(ii) In the specimen test automation system 100 described above, the transport device 102 and the analyzer 103 are a set, but the technology in the present disclosure is applicable to a configuration in which the transport device 102 is omitted and a single or a plurality of analyzers 103 are connected, or a configuration in which the analyzer 103 is omitted and a single or a plurality of transport devices 102 are connected.

(iii) After an IP address is allocated to each unit and the specimen test automation system 100 is set, when the power of the entire system is turned off (the system configuration is reset) and then the power of the system is turned on again, the above-described operation may be performed again to reconfigure the system. Alternatively, after system setting is completed once, the operation unit PC 101 may store a result, and when power of each unit is turned on again, a start completion signal may be sequentially output to each unit based on the stored IP address, and the IP address allocation processing is omitted. When there is a change such as an addition of a unit, an operation such as ID setting is performed on each unit again.

(iv) In the IP address allocation method 1 as well, as in the IP address allocation method 2 to be described later, the operation unit PC 101 may acquire the path information on each slave station device (the transport device 102 and the analyzer 103: each unit).

(2) IP Address Allocation Method 2

The IP address allocation method 2 relates to a method of acquiring path information on each unit (the transport device 102 and the analyzer 103) constituting the specimen test automation system 100 without referring to an IP address table (design information) held in the LIS 105 in advance and allocating an IP address to a write unit based on the path information. Hereinafter, the IP address allocation method 2 will be described in detail. As a configuration of a specimen test automation system that executes the IP address allocation method 2, the specimen test automation system 100 described in the IP address allocation method 1 can be adopted. Therefore, the description of the configuration example of the specimen test automation system 100 is omitted here.

<Path Information Acquisition Processing>

FIG. 5 is a diagram showing an example of a system configuration of the IP address allocation target, and an example of a connection configuration of the operation unit PC (master station device) 101 and a plurality of units (slave station devices: transport devices 102_1 to n and analyzers 103_1 to m; n and m are any integers). FIG. 6 is a diagram showing a part of a path information table acquired by the path information acquisition processing.

When setup of the specimen test automation system 100 is completed and the system power is turned on, a central control unit (processor 1011) of the operation unit PC (management device) 101 is started up, and an IP address allocation function of each slave station device is started. For the path information acquisition processing, a plurality of types of methods are conceivable as follows, but this is merely an example, and any method may be adopted as long as a path from the operation unit PC 101 to each unit is understood.

(i) Path Information Acquisition Processing Example 1

The operation unit PC 101 sequentially transfers an empty packet 501 to all the units. To show the system configuration in FIG. 5 as an example, the operation unit PC 101 first transmits the empty packet 501 to the directly connected transport device A 102_1. The transport device A 102_1 that receives the empty packet 501 allocates a port number (port number 2 in the example in FIG. 5) of the Ethernet cable 104 connected to the operation unit PC 101 to a path information register unit of the empty packet 501, allocates (adds) information indicating presence or absence of a unit downstream connected to the unit itself to the empty packet 501, and transmits the empty packet 501 to a device upstream (operation unit PC 101). Upon receiving a packet 501' to which a port number is allocated from the transport device A 102_1, the operation unit PC 101 stores "21" as path information on the transport device A 102_1 in the path information table (FIG. 6). Here, "2" indicates a port number of the transport device A 102_1, and "1" indicates the operation unit PC 101 itself. That is, "21" indicates that the transport device A 102_1 is connected to the operation unit PC 101 via the port number 2. When the packet 501' received from the transport device A 102_1 indicates that another slave station device (transport device B 102_2 in FIG. 5) is connected downstream of the transport device A 102_1, the operation unit PC 101 transmits the empty packet 501 to the slave station device (transport device B 102_2) via the transport device A 102_1. The transport device B 102_2 allocates a port number (port number 2 in the example in FIG. 5) of the Ethernet cable 104 connected to the transport device A 102_1 to the path information register unit of the empty packet 501, allocates (adds) information indicating presence or absence of a unit downstream connected to the unit itself to the empty packet 501, and transmits the empty packet 501 to the transport device A 102_1. The transport device A 102_1 allocates the port number (port number 2) to which the Ethernet cable 104 is connected upstream to the packet 501' received from the transport device B 102_2, and transmits the packet 501' to the device upstream (operation unit PC 101). Upon receiving the packet 501' to which the port number is allocated from the transport device A 102_1, the operation unit PC 101 stores "221" as path information on the transport device B 102_2 in the path information table (FIG. 6). Here, a leftmost "2" indicates a port number of the transport device B 102_2, a middle "2" indicates the port number of the transport device A 102_1, and a rightmost "1" indicates the operation unit PC 101 itself. That is, "221" indicates that the transport device B 102_2 is connected to the transport device A 102_1 via the port number 2 and the transport device A 102_1 is connected to the operation unit PC 101 via the port number 2. Further, similar processing is repeated up to the analyzer A 103_1 to which no other unit is connected downstream.

The operation unit PC 101 transmits the empty packet 501 to the transport device C 102_3, which is different from the transport device A 102_1 directly connected thereto. The transport device C 102_3 that receives the empty packet 501 allocates a port number (port number 3 in the example in FIG. 5) of the Ethernet cable 104 connected to the operation unit PC 101 to the path information register unit of the empty packet 501, allocates (adds) information indicating presence or absence of a unit downstream connected to the unit itself to the empty packet 501, and transmits the empty packet 501 to a device upstream (operation unit PC 101). Upon receiving the packet 501' to which the port number is allocated from the transport device C 102_3, the operation unit PC 101 stores "31" as path information on the transport device C 102_3 in the path information table (FIG. 6). Here, "3" indicates a port number of the transport device C 102_3, and "1" indicates the operation unit PC 101 itself. That is, "31" indicates that the transport device C 102_3 is connected to the operation unit PC 101 via the port number 3. When the packet 501' received from the transport device C 102_3 indicates that another slave station device (transport device D 102_4 in FIG. 5) is connected downstream of the transport device C 102_3, the operation unit PC 101 transmits the empty packet 501 to the slave station device (transport device D 102_4) via the transport device C 102_3. The transport device D 102_4 allocates a port number (port number 2 in the example in FIG. 5) of the Ethernet cable 104 connected to the transport device C 102_3 to the path information register unit of the empty packet 501, allocates (adds) information indicating presence or absence of a unit downstream connected to the unit itself to the empty packet 501, and transmits the empty packet 501 to the transport device C 102_3. The transport device C 102_3 allocates the port number (port number 2) to which the Ethernet cable 104 is connected upstream to the packet 501' received from the transport device D 102_4, and transmits the packet 501' to the device upstream (operation unit PC 101). Upon receiving the packet 501' to which the port number is allocated from the transport device C 102_3, the operation unit PC 101 stores "231" as path information on the transport device D 102_4 in the path information table (FIG. 6). Here, a leftmost "2" indicates a port number of the transport device D 102_4, a middle "3" indicates the port number of the transport device C 102_3, and a rightmost "1" indicates the operation unit PC 101 itself. That is, "231" indicates that the transport device D 102_4 is connected to the transport device C 102_3 via the port number 2 and the transport device C 102_3 is connected to the operation unit PC 101 via the port number 3. Further, similar processing is repeated up to the analyzer B 103_2 to which no other unit is connected downstream.

Further, when the packet 501' from the transport device D 102_4 includes information indicating that a plurality of slave station devices are connected (in the example in FIG. 5, the analyzer B 103_2 and the transport device E 102_5), after a path to the analyzer B 103_2 is acquired, the operation unit PC 101 transmits the empty packet 501 to the transport device E 102_5 via the transport device C 102_3 and the transport device D 102_4. The transport device E 102_5 that receives the empty packet 501 allocates a port number (port number 3 in the example in FIG. 5) of the Ethernet cable 104 connected to the transport device D 102_4 to the path information register unit of the empty packet 501, allocates (adds) information indicating presence or absence of a unit downstream connected to the unit itself to the empty packet 501, and transmits the empty packet 501 to a device upstream (transport device D 102_4). The transport device D 102_4 allocates the port number (port number 2) to which the Ethernet cable 104 is connected upstream to the packet 501' received from the transport device E 102_5, and transmits the packet 501' to the device upstream (transport device C 102_3). Upon receiving the packet 501' to which the port number is allocated from the transport device D 102_4, the transport device C 102_3 further allocates, to the packet 501', the port number (port number 3 in the example in FIG. 5) to which the device upstream (operation unit PC 101) is connected and transmits the packet 501' to the operation unit PC 101. Upon receiving the packet 501' to which the port number is allocated from the transport device C 102_3, the operation unit PC 101 stores "3231" as path information on the transport device E 102_5 in the path information table (FIG. 6). Here, a leftmost "3" indicates a port number of the transport device E 102_5, a second "2" from a left indicates the port number of the transport device D 102_4, a third "3" from the left indicates the port number of the transport device C 102_3, and a rightmost "1" indicates the operation unit PC 101 itself. That is, "3231" indicates that the transport device E 102_5 is connected to the transport device D 102_4 via the port number 3, the transport device D 102_4 is connected to the transport device C 102_3 via the port number 2, and the transport device C 102_3 is connected to the operation unit PC 101 via the port number 3. Further, similar processing is repeated up to the analyzer C 103_3 to which no other unit is connected downstream.

(ii) Path Information Acquisition Processing Example 2

First, the operation unit PC 101 executes communication with each of the slave station devices (units: the transport devices A to E, 102_1 to 5, and the analyzers A to C, 103_1 to 3) (for example, transmits an inquiry signal from the operation unit PC 101 in the first communication mode and responds to the inquiry in the second communication mode), and acquires information on positions of units having branches in an X-axis (horizontal) direction and a Y-axis (vertical) direction (how many units from the operation unit PC 101 in vertical and horizontal directions) when the operation unit PC 101 is an origin.

Then, the operation unit PC 101 sequentially or simultaneously transmits the empty packets 501 for the number of units having branches +1. In the system configuration in FIG. 5, since the units having branches are the operation unit PC 101 itself and the transport device C 102_5, three empty packets 501 are transmitted from the operation unit PC 101. The first empty packet 501 is transmitted via the transport device A 102_1 and the transport device B 102_2 to the analyzer A 103_1 to which no slave station device is connected downstream. Upon receiving the empty packet 501, the analyzer A 103_1 allocates the port number 2 to which the transport device B 102_2 (unit upstream) is connected to the path information register unit of the empty packet 501, and transmits the empty packet 501 to the transport device B 102_2 (unit upstream) as the packet 501'. Upon receiving the packet 501', the transport device B 102_2 allocates the port number 2 to which the transport device A 102_1 is connected to the port number allocated by the analyzer A 103_1, and transmits the packet 501' to the transport device A 102_1 (unit upstream). Upon receiving the packet 501' from the transport device B 102_2 (unit downstream), the transport device A 102_1 allocates, to the packet 501', the port number 2 to which the operation unit PC 101 (unit upstream) is connected and transmits the packet 501' to the operation unit PC 101 (unit upstream). Upon receiving the packet 501', the operation unit PC 101 allocates its own port number 1 to a port number sequence in the packet 501', thereby setting a path to the analyzer A 103_1 (for example, 2221), and stores the path in the path information table (FIG. 6). Since the operation unit PC 101 can recognize the path to the unit that is present between the operation unit PC 101 and the analyzer A 103_1 by acquiring path information to the analyzer A 103_1, the operation unit PC 101 also stores the path information (the path 21 to the transport device A 102_1 and the path 221 to the transport device B 102_2) in the path information table.

The second empty packet 501 is transmitted via the transport device C 102_3 and the transport device D 102_4 to the analyzer B 103_2. Similar processing as in the case of the first empty packet 501 is performed, and a path (for example, 2231) to the analyzer B 103_2 is stored in the path information table. Similarly, paths ("31" and "231") to the transport device C 102_3 and the transport device D 102_4 between the operation unit PC 101 and the analyzer B 103_2 are obtained and stored in the path information table.

Further, the third empty packet 501 is transmitted via the transport device C 102_3, the transport device D 102_4, and the transport device E 102_5 to the analyzer 103_3. Similar processing is performed for the first and second empty packets 501, and a path (for example, 23231) to the analyzer C103_3 is obtained. Since the path to the transport device C 102_3 and the path to the transport device D 102_4 can be grasped by the transmission of the second empty packet 501, the path to the transport device E 102_5 (for example, 3231) is obtained and added to the path information table.

(iii) Setting of Main Path and Sub Path Based on Path Information

When the operation unit PC 101 acquires the path information as described above, the operation unit PC 101 can determine whether there is a branch in the path and determine a unit group constituting the main path. For example, in a configuration of the specimen test automation system 100 in FIG. 5, the transport device A 102_1→the transport device B 102_2→the analyzer A 103_1 can be determined as the main path. The operation unit PC 101 determines a unit group constituting the sub path. For example, in the system configuration in FIG. 5, a sub path 1, which is the operation unit PC 101→the transport device C 102_3→the transport device D 102_4→the analyzer B 103_2, and a sub path 2, which is the operation unit PC 101→the transport device C 102_3→the transport device D 102_4→the transport device E 102_5→the analyzer C103_3, are determined. The sub path 1 may be the main path, and the other paths may be the sub path 1 and the sub path 2. At this time, in the IP address allocation processing, it can be defined that the sub path 1 has a priority over the sub path 2.

Based on the path information acquired as described above (the path information can be path information related to all the units including one main path and at least one sub path), IP address allocation processing according to the IP address allocation method 2 is executed as described below (see FIG. 7).

<Content of IP Address Allocation Processing 2>

FIG. 7 is a flowchart showing the IP address allocation processing according to the IP address allocation method 2.

(i) Step 701

When the operation unit PC 101 completes acquiring the path information (see FIG. 6) on each slave station device (each unit), the operation unit PC 101 starts allocating an IP address to each unit.

(ii) Step 702

The operation unit PC 101 refers to the path information stored in the path information table (FIG. 6) to allocate the acquired path information to a path information unit of the empty packet 501, and allocates an IP address=1 (here, the IP address is set to 1, but a desired address can be used) to an IP address unit. The operation unit PC 101 transmits the packet 501 filled with the IP address to the units (the transport device A 102_1 and the transport device C 102_3 in FIG. 5) connected downstream.

(iii) Step 703

Upon receiving the packet 501 to which the IP address=1 is allocated, the unit downstream (slave station device: the transport device A 102_1 or the transport device C 102_3 in the case of first processing) stores the IP address in the storage device 1022 (the storage device 1032 when an allocation target is the analyzer 103) as its own IP address.

(iv) Step 704

After storing the IP address in the storage device 1022 (or the storage device 1032), the unit (slave station device)

determines whether another unit (unit downstream) is connected downstream thereof in the path information in the packet 501. Presence or absence of a connection to a unit downstream can be determined based on, for example, whether the path information in the packet includes a port number of another unit that follows the unit (own unit). Alternatively, for example, presence or absence of a connection to a unit downstream can be determined by the processor 1021 or 1031 of the unit transmitting a connection confirmation signal to each port of the unit and receiving an Ack signal from a unit downstream as a connection destination. Further, for example, when the unit downstream of the unit is connected, the processor 1021 or 1031 may recognize the connection of the unit downstream and a connection port number. In the above-described path information acquisition processing, each unit may recognize whether the unit itself is connected to a unit downstream, and information thereof may be stored in the storage device 1022 or 1032.

When it is determined that there is no connection to the unit downstream (NO in step 704), the processing proceeds to step 705. Meanwhile, when it is determined that there is a connection to the unit downstream (YES in step 704), the processing proceeds to step 711.

(v) Step 705

The unit (for example, the analyzer A 103_1 having no connection to another unit downstream) reports completion of IP address allocation to the unit, and transfers the received packet 501 to a unit upstream (for example, the transport device B 102_2). In FIG. 7, steps 705 to 707 are loop processing, and in a case of a system example in FIG. 5, a first transfer is from the analyzer A 103_1 to the transport device B 102_2, but in second and subsequent loop processing, the units upstream are the transport device A 102_1 and the operation unit PC 101.

(vi) Step 706

The unit upstream (for example, the transport device B 102_2) receives the packet 501 from the unit downstream (for example, the analyzer A 103_1), and stores an IP address stored in the received packet 501 as an IP address of the unit downstream (in the storage device 1022 in the case of the transport device B 102_2).

(vii) Step 707

The unit upstream (for example, the transport device B 102_2) determines whether there is a connection of the unit upstream to the self device. When there is a connection of a unit upstream to the self device (YES in step 707), the processing returns to step 705. Meanwhile, when there is no connection of the unit upstream to the self device (NO in step 707), the processing proceeds to step 708. For example, in the case of the transport device B 102_2, since the transport device A 102_1 is further present as a unit upstream, YES is determined in step 707, and the processing returns to step 705.

(viii) Step 708

The operation unit PC 101 determines whether the IP address allocation processing is completed for all the units (slave station devices) in the acquired path information. When IP address allocation to all the units is completed (YES in step 708), the processing proceeds to step 709. Meanwhile, when the IP address allocation to all the units is not completed (NO in step 708), the processing proceeds to step 710.

(ix) Step 709

Since the allocation of the IP address to all the units in the specimen test automation system 100 is completed, the processing is completed by the IP address allocation method 2.

(x) Step 710

The operation unit PC 101 instructs a branch source unit (for example, the operation unit PC 101 itself or the transport device D 102_4 in FIG. 5) to start IP address allocation processing, and causes the processing to proceed to step 712.

(xi) Step 711

The unit downstream that receives the packet 501 in step 703 (for example, the transport device A to E, 102_1 to 5, in FIG. 5) determines whether there is a branch connection to the self device. Presence or absence of the branch connection can be determined, for example, based on the path information allocated to the packet (information indicating in which part a branch is present may be included). Alternatively, for example, the presence or absence of the branch connection can be determined by the processor 1021 or 1031 of the unit transmitting a connection confirmation signal to each port of the unit and checking whether two or more Ack signals are received. Further, for example, when a plurality of units downstream of the unit are connected, the processor 1021 or 1031 may recognize presence or absence of a branch and a port number to which the unit downstream is connected. In the above-described path information acquisition processing, the presence or absence of a branch connection in each unit may be recognized, and the information may be stored in the storage device 1012, 1022, or 1032.

When the unit downstream has a branch connection (YES in step 711), the processing proceeds to step 712. When the unit downstream does not have a branch connection (NO in step 711), the processing proceeds to step 714.

In the specimen test automation system 100 in FIG. 5, in the case of the main path, since there is no branch connection, the processing proceeds to step 714. Meanwhile, for example, when it is determined whether there is a branch connection at the transport device D 102_4 in the sub path 1, the processing proceeds to step 712.

(xii) Step 712

The branch source unit (for example, the operation unit PC 101 or the transport device D 102_4) determines whether an IP address allocated to a final stage unit (for example, the analyzer A 103_1 or the analyzer B 103_2) in the path having one higher priority (for example, the main path or the sub path 1) is stored. When the branch source unit stores the IP address of the final stage unit in the path having one higher priority (YES in step 712), the processing proceeds to step 713. Meanwhile, when the branch source unit does not store the IP address of the final stage unit in the path having one higher priority (NO in step 712), the processing proceeds to step 715.

For example, when the processing from step 705 to step 709 is completed and the IP address allocation is already completed for a path having a high priority (for example, the main path or the sub path 1), the branch source unit holds an IP address of the final stage unit (the analyzer A 103_1 or the analyzer B 103_2) in the path having one higher priority (the main path for the sub path 1 or the sub path 1 for the sub path 2). Therefore, YES is determined in step 712, and the processing proceeds to step 713. Meanwhile, when the IP address allocation to each unit in the path having the one higher priority is not completed, the determination in step 712 is NO, and the processing proceeds to step 715.

(xiii) Step 713

The branch source unit (for example, the operation unit PC 101 or the transport device D 102_4) transmits IP address of the final stage unit in the path having one higher priority +1 to a branch destination unit (for example, the transport device C 102_3 in the sub path 1 or the transport device E 102_5 in the sub path 2). Subsequently, the processing proceeds to step 703. At this time, the "unit downstream" in step 703 means the branch destination unit.

(xiv) Step 714

The unit downstream having no branch connection (for example, the transport device A 102_1 or the transport device B 102_2 downstream of the operation unit PC 101 in the main path in FIG. 5) transmits an IP address, which is an IP address that is transmitted thereto +1, to a unit downstream (for example, the transport device B 102_2 for the transport device A 102_1 or the analyzer A 103_1 for the transport device B 102_2). Subsequently, the processing proceeds to step 703. At this time, the "unit downstream" in step 703 means, for example, the transport device B 102_2 for the transport device A 102_1 or the analyzer A 103_1 for the transport device B 102_2.

(xv) Step 715

The branch source unit (for example, the transport device D 102_4) that does not acquire the IP address of the final stage unit (for example, the analyzer B 103_1) in the path having one higher priority (for example, the sub path 1 in FIG. 5) transmits the IP address, which is its own IP address +1 to the unit downstream (for example, the analyzer B 103_2).

<Summary of IP Address Allocation Method 2>

(i) As described above, according to the IP address allocation method 2 in the present embodiment, it is possible to easily and automatically allocate an IP address to each unit, similarly to the above-described IP address allocation method 1. When there are a plurality of transport devices and analyzers having the same function, the transport devices and the analyzers can be freely disposed without considering the disposition positions. When the disposition direction is not limited by a hardware configuration such as in the case of the bilaterally symmetrical device configuration, the directions of the transport device and the analyzer can be freely disposed. Unlike the IP address allocation method 1 described above, an IP address can be automatically allocated to each unit without requiring design information. A switch (for example, a push button switch) for turning on the power of the specimen test automation system 100 may be pressed by an operator such as a service person, or the switch may be automatically turned on by turning on power of the operation unit PC 101.

(ii) In the specimen test automation system 100 that executes the IP address allocation method 2 as well, the transport device 102 and the analyzer 103 are a set, but the technology in the present disclosure is applicable to a configuration in which the transport device 102 is omitted and a single or a plurality of analyzers 103 are connected, or a configuration in which the analyzer 103 is omitted and a single or a plurality of transport devices 102 are connected.

(iii) In the IP address allocation method 2 as well, after an IP address is allocated to each unit and the specimen test automation system 100 is set, when the power of the entire system is turned off (the system configuration is reset) and then the power of the system is turned on again, the above-described operation may be performed again to reconfigure the system. Alternatively, after the system setting is completed once, the operation unit PC 101 may store a result, and when the power of each unit is turned on again, a start completion signal may be sequentially output to each unit based on the stored IP address, and the IP address allocation processing is omitted. When there is a change such as an addition of a unit, an operation such as ID setting is performed on each unit again.

(iv) Modification

In the processing shown in the flowchart in FIG. 7, the path information indicating a connection relationship of all the units is in the packet 501, but the invention is not limited thereto, and the packet 501 may include the main path or the sub path as the path information. In this case, when the IP address allocation processing for each unit in one path (main path and each sub path: each path may be given a priority) of the system is completed, the operation unit PC 101 can restart the IP address allocation processing from a unit having a branch connection in a path (a path having a next priority) of a next system.

(3) IP Address Consistency Check Processing

The IP address consistency check processing is processing of checking consistency of a unit IP address (an IP address allocated to each unit by the IP address allocation method 1 or 2) allocated by the operation unit PC 101 (processing of checking whether the IP address allocation processing functions normally). Specifically, the IP address consistency check processing is processing of checking consistency of a result based on the IP address allocation method 1 using the IP address allocation method 2 and checking consistency of the result based on the IP address allocation method 2 using design information. Hereinafter, details thereof will be described with reference to FIG. 8. FIG. 8 is a flowchart showing details of the IP address consistency check processing.

(i) Step 801

The operation unit PC 101 completes the allocation of the IP address to each unit (slave station device) in the specimen test automation system 100, and then starts the consistency check processing of the IP address.

(ii) Step 802

The operation unit PC 101 determines whether the IP address of each unit is allocated by referring to the design information, that is, allocated according to the IP address allocation method 1. When the IP address is allocated with reference to the design information (YES in step 802), the processing proceeds to step 803. Meanwhile, when the IP address is allocated without referring to the design information (NO in step 802), the processing proceeds to step 805.

(iii) Step 803

The operation unit PC 101 acquires path information on each unit constituting the specimen test automation system 100. The path information acquisition processing is as described above.

(iv) Step 804

The operation unit PC 101 cooperates with each unit (slave station device) to determine an IP address of each unit. The IP address of each unit is determined according to the IP address allocation method 2 (FIG. 7).

(v) Step 805

The operation unit PC 101 acquires design information (see FIG. 3). When the operation unit PC 101 does not hold design information in the storage device 1012 in advance, the design information is acquired from the LIS 105. When the design information is not held in the LIS 105, the operation unit PC 101 may output information indicating that the design information cannot be acquired to the output device (for example, the display device) 1014 to prompt the operator (user) to input the design information.

(vi) Step 806

When an IP address is allocated to each unit with reference to the design information (according to the IP address allocation method 1), the operation unit PC 101 compares the IP address based on the design information with the IP address determined in step 804. Meanwhile, when the IP address is allocated to each unit without referring to the design information (according to the IP address allocation method 2), the operation unit PC 101 compares the IP address not based on the design information with the design information acquired in step 805. When there is no difference between the compared IP addresses (NO in step 806), the processing proceeds to step 808. When there is a difference between the compared IP addresses (YES in step 806), the processing proceeds to step 807.

(vii) Step 807

The operation unit PC 101 ends the IP address consistency check processing and starts an operation of the specimen test automation system 100.

(viii) Step 808

The operation unit PC 101 outputs to the output device 1014 (for example, displays on a display screen of a display device) that the IP addresses allocated to the unit are not consistent (alarm). The operator (user) recognizes an output alarm content, confirms the design information held by the LIS 105 and an actual connection, and specifies a cause of an IP address allocation error.

(ix) Others

Contents of the IP address consistency check processing shown in FIG. 8 are merely examples, and can be flexibly changed according to the configuration of the specimen test automation system 100.

(4) Overview (i) The specimen test automation system 100 in the present embodiment conforms to the distributed control method, and includes a plurality of slave station devices (units: the transport device 102 and the analyzer 103), and a master station device (the operation unit PC 101) configured to communicate with the plurality of slave station devices via the communication path and control the plurality of slave station devices. In such a configuration, the master station device executes, using information acquired by communicating with each of the plurality of slave station devices (a communication path (a first communication path: the first communication mode) from the master station device to the slave station device and a communication path (a second communication path: the second communication mode) from a slave station device to a slave station device or the master station device upstream are separately provided), processing of allocating unique position information (IP address) to each of the plurality of slave station devices. In this way, the operator (user) can construct a system by arranging the units as appropriate, and after that, the master station device allocates an IP address from each of the slave station devices, thereby easily and flexibly implementing the specimen test automation system without considering a disposition of each of the slave station devices (which unit is to be disposed at which position).

In the specimen test automation system 100, a direction toward the plurality of slave station devices (units) as viewed from the master station device (the operation unit PC 101) is defined as downstream, and a direction toward the master station device as viewed from the plurality of slave station devices (units) is defined as upstream. At this time, each communication path has the first communication path (first communication mode) through which the master station device can transmit a control command to each of the slave station devices from upstream to downstream, and the second communication path (second communication mode) through which the plurality of slave station devices can transmit a control command to the master station device from downstream to upstream. By dividing the communication path, information can be exchanged in parallel between the master station device and each slave station device.

(ii) According to the IP address allocation method 1 in the present embodiment, when the master station device (the operation unit PC 101) receives an allocation request of the unique position information (for example, the IP address) including the identification information for specifying each of the slave station devices from the plurality of slave station devices (the units: the transport device 102 and the analyzer 103), the master station device allocates the unique position information to the plurality of slave station devices based on given design information on the specimen test automation system 100 (for example, FIG. 3: information set in advance and indicating a layout of the units in the specimen test automation system 100) and the identification information. More specifically, the master station device determines the unique position information on the plurality of slave station devices based on information on the priority order in the design information. The master station device transmits the determined unique position information to each of the plurality of slave station devices using the identification information on the plurality of slave station devices. When receiving the unique position information including the identification information, each of the slave station devices stores the unique position information stored in the packet including one's own identification information in one's own storage device. In this way, the user can automatically construct the specimen test automation system without considering a layout and order of the units. It is not necessary to allocate fixed unique position information (IP address) to each unit in advance.

(iii) According to the IP address allocation method 2 in the present embodiment, the master station device acquires the path information on each slave station device by communicating with the plurality of slave station devices, and allocates the unique position information to each of the plurality of slave station devices in an order of paths in the acquired path information. More specifically, the master station device transmits, to a first slave station device downstream (a unit as the IP address allocation target), a packet including the path information and first unique position information to be allocated. The first slave station device stores the first unique position information in the packet in its own storage device, and when a second slave station device is further connected downstream of the first slave station device, transmits, to the second slave station device, a packet including second unique position information obtained by adding a predetermined value to the first unique position information. Further, when a third slave station device is further connected downstream of the second slave station device, the second slave station device transmits, to the third slave station device, a packet including third unique position information obtained by adding a predetermined value to the second unique position information. In this way, the unique position information (IP address) can be sequentially and automatically allocated to the units downstream along the path, so that the user can easily construct the specimen test automation system 100.

The IP address allocation method 2 in the present embodiment also deals with a case where a system path has a branch. For example, the master station device transmits, to the first slave station device downstream, a packet including the path information and the first unique position information to be allocated. However, at this time, the first slave station device stores the first unique position information in the packet in its own storage device, and when the first slave station device has a branch connection, the first slave station device determines whether final stage unique position information is held, which is allocated to a slave station device at a final stage in a path having a high priority in the path information. The first slave station device executes allocation of unique position information to the slave station device based on a determination result. More specifically, when the first slave station device having the branch connection (i) does not hold the final stage unique position information, the first slave station device executes allocation of the unique position information to a slave station device in a path having a high priority. Meanwhile, when the first slave station device (ii) holds the final stage unique position information, the first slave station device adds a predetermined value to the final stage unique position information to generate updated unique position information, and transmits the updated unique position information to a slave station device as the branch destination. In this way, even when there is a branch in the path of the specimen test automation system 100, it is possible to automatically allocate the unique position information to each unit easily and reliably.

(iv) The present embodiment also proposes a method of confirming whether the unique position information (IP address) allocated to each slave station device (unit) by the IP address allocation method 1 or 2 is correct. For example, when the unique position information is allocated to each slave station device by the IP address allocation method 2 (a method of allocating the unique position information to each unit based on the path information), the unique position information is compared with unique position information based on the design information (unique position information allocated according to the IP address allocation method 1). In this way, it is possible to confirm whether the unique position information allocation according to the IP address allocation method 1 is correctly executed.

Meanwhile, for example, when the unique position information is allocated to each slave station device by the IP address allocation method 1 (a method of allocating the unique position information to each unit based on the design information), the unique position information allocated to each of the slave station devices is obtained separately according to the IP address allocation method 2. Then, the unique position information by the IP address allocation method 1 is compared with the unique position information by the IP address allocation method 2. In this way, it is possible to confirm whether the unique position information allocation according to the IP address allocation method 2 is correctly executed.

(v) A function of the present embodiment can also be implemented by a software program code. In this case, a storage medium in which the program code is recorded is provided to the system or device, and a computer (or CPU or MPU) of the system or device reads the program code stored in the storage medium. In this case, the program code itself read from the storage medium implements the function of the above-described embodiment, and the program code itself and the storage medium storing the program code constitute the present disclosure. Examples of the storage medium for supplying such a program code include a flexible disk, a CD-ROM, a DVD-ROM, a hard disk, an optical disk, a magneto-optical disk, a CD-R, a magnetic tape, a nonvolatile memory card, and a ROM.

An operating system (OS) or the like operating on a computer may perform a part or all of actual processing based on an instruction of a program code, and the function of the above-described embodiment may be implemented by the processing. Further, after the program code read from the storage medium is written in the memory on the computer, the CPU or the like of the computer may perform a part or all of the actual processing based on the instruction of the program code, and the function of the above-described embodiment may be implemented by the processing.

Further, the software program code for implementing the function of the present embodiment may be distributed via a network and stored in a storage unit such as a hard disk or a memory of the system or the device or a storage medium such as a CD-RW or a CD-R, and the computer (or CPU or MPU) of the system or the device may read and execute the program code stored in the storage unit or the storage medium at the time of use.

Finally, processes and techniques described here are not essentially related to any specific device, and can be implemented by any appropriate combination of components. Further, various types of devices for general purposes can be used in accordance with teachings described here. It may prove advantageous to construct a dedicated device to execute the steps of the method described here. Various forms can be formed by appropriately combining a plurality of components disclosed in the present embodiment. For example, several components may be deleted from all the components shown in the present embodiment. Further, components belonging to different embodiments may be appropriately combined. Although the present disclosure is described in relation to specific examples, the present disclosure is not to be limited in all viewpoints. It is understood that there are many combinations of hardware, software, and firmware suitable for implementing the technology of the present disclosure for persons having ordinary knowledge in the present technical field (those skilled in the art). For example, the described software can be implemented in a wide range of programs or script languages such as assembler, C/C++, perl, Shell, PHP, and Java (registered trademark).

Further, control lines and information lines considered to be necessary for description are shown in the embodiments described above, and not all control lines and information lines in a product are necessarily shown. All the configurations may be connected to one another.

REFERENCE SIGNS LIST

100: specimen test automation system
101: operation unit PC
102: transport device
102_1: transport device A
102_2: transport device B
102_3: transport device C
102_4: transport device D
102_5: transport device E
103: analyzer
103_1: analyzer A
103_2: analyzer B
103_3: analyzer C
104: Ethernet cable
105: laboratory information system (LSI)
501: packet

The invention claimed is:

1. A specimen test automation system comprising:

a plurality of slave station devices each corresponding to at least one of a transport device that transports a specimen and an analyzer that analyzes the specimen; and a master station device configured to communicate with the plurality of slave station devices via a communication path and control the plurality of slave station devices, wherein when a direction toward the plurality of slave station devices as viewed from the master station device is defined as downstream, and a direction toward the master station device as viewed from the plurality of slave station devices is defined as upstream, the communication path has a first communication path through which the master station device is configured to transmit a control command to each of the slave station devices from upstream to downstream, and a second communication path through which the plurality of slave station devices is configured to transmit a control command to the master station device from downstream to upstream, the master station device acquires path information on each slave station device by communicating with the plurality of slave station devices, and allocates the unique position information to each of the plurality of slave station devices in an order of paths in the acquired path information, the master station device transmits, to a first slave station device downstream, a packet including the path information and first unique position information to be allocated, and the first slave station device stores the first unique position information in the packet in its own storage device, and when a second slave station device is further connected downstream of the first slave station device, transmits, to the second slave station device, a packet including second unique position information obtained by adding a predetermined value to the first unique position information.

2. The specimen test automation system according to claim 1, wherein the plurality of slave station devices each have a plurality of ports each having a reception terminal and a transmission terminal for connecting to a slave station device other than the slave station device itself, a disposition of transmission terminals and reception terminals in a port for connecting to another slave station device upstream or the master station device and a port for connecting to another slave station device downstream is unified, and the ports are connected to each other via a cross cable.

3. The specimen test automation system according to claim 1, wherein when a third slave station device is further connected downstream of the second slave station device, the second slave station device transmits, to the third slave station device, a packet including third unique position information obtained by adding a predetermined value to the second unique position information.

4. The specimen test automation system according to claim 1, wherein the master station device acquires design information including information on disposition positions of the master station device and the plurality of slave station devices in the specimen test automation system, compares the design information with unique position information based on the path information, checks consistency of unique position information allocated to each of the plurality of slave station devices, and outputs a result of the check.

5. The specimen test automation system according to claim 1, wherein the master station device transmits, to the first slave station device downstream, a packet including the path information and the first unique position information to be allocated, the first slave station device stores the first unique position information in the packet in its own storage device, and when the first slave station device has a branch connection, the first slave station device determines whether final stage unique position information is held, which is allocated to a slave station device at a final stage in a path having a high priority in the path information, and the first slave station device executes allocation of unique position information to the slave station device based on a determination result.

6. The specimen test automation system according to claim 5, wherein when the first slave station device having the branch connection (i) does not hold the final stage unique position information, the first slave station device executes allocation of the unique position information to a slave station device in a path having the high priority, and when the first slave station device having the branch connection (ii) holds the final stage unique position information, the first slave station device adds a predetermined value to the final stage unique position information to generate updated unique position information, and transmits the updated unique position information to a slave station device as a branch destination of the first slave station device having the branch connection.

7. The specimen test automation system according to claim 1, wherein when the master station device receives an allocation request of the unique position information including identification information for specifying each of the slave station devices from the plurality of slave station devices, the master station device allocates the unique position information to the plurality of slave station devices based on given design information on the specimen test automation system and the identification information.

8. The specimen test automation system according to claim 7, wherein the master station device determines the unique position information on the plurality of slave station devices based on information on a priority order in the design information, and transmits the determined unique position information to each of the plurality of slave station devices using the identification information on the plurality of slave station devices, and the plurality of slave station devices store the unique position information corresponding to one's own identification information in one's own storage device.

9. The specimen test automation system according to claim 7, wherein the master station device acquires path information on each slave station device by communicating with the plurality of slave station devices, generates unique position information based on the path information allocated to each of the plurality of slave station devices in an order of paths in the acquired path information, compares unique position information based on the given design information with unique position information based on the path information, checks consistency of unique position information allocated to each of the plurality of slave station devices, and outputs a result of the check.

10. A fixed position information allocation method of allocating unique position information to a plurality of slave station devices in a specimen test automation system, the specimen test automation system including the plurality of slave station devices each corresponding to at least one of a transport device that transports a specimen and an analyzer that analyzes the specimen, and a master station device configured to communicate with the plurality of slave station devices via a communication path and control the plurality of slave station devices, wherein when a direction toward the plurality of slave station devices as viewed from the master station device is defined as downstream, and a direction toward the master station device as viewed from the plurality of slave station devices is defined as upstream, the communication path has a first communication path through which the master station device is configured to transmit a control command to each of the slave station devices from upstream to downstream, and a second communication path through which the plurality of slave station devices is configured to transmit a control command to the master station device from downstream to upstream, and the fixed position information allocation method comprises:

acquiring, by the master station device, path information on each slave station device by communicating with the plurality of slave station devices, and allocating, by the master station device, the unique position information to each of the plurality of slave station devices in an order of paths in the acquired path information;

transmitting, by the master station device, to a first slave station device downstream, a packet including the path information and first unique position information to be allocated; and storing, by the first slave station device, the first unique position information in the packet in its own storage device, and when a second slave station device is further connected downstream of the first slave station device, transmitting, by the first slave station device, to the second slave station device, a packet including second unique position information obtained by adding a predetermined value to the first unique position information.

11. The method according to claim 10, wherein acquiring the predetermined information includes receiving, by the master station device, an allocation request for the unique position information including identification information for specifying each of the plurality of slave station devices from the plurality of slave station devices, and allocating the unique position information includes allocating, by the master station device, the unique position information to the plurality of slave station devices based on given design information on the specimen test automation system and the identification information.

12. The method according to claim 10, wherein acquiring the predetermined method includes acquiring path information on each slave station device by the master station device communicating with the plurality of slave station devices, and allocating the unique position information includes allocating the unique position information to each of the plurality of slave station devices in an order of paths in the acquired path information.

* * * * *